United States Patent [19]

Okonogi et al.

[11] Patent Number: 4,888,171
[45] Date of Patent: Dec. 19, 1989

[54] GRANULAR PRODUCT OF DRIED MICROORGANISM CELLS AND MANUFACTURING METHOD THEREFOR

[75] Inventors: Shigeo Okonogi, Ohta; Mamoru Tomita; Seiichi Shimamura, both of Yokohama; Norio Ishibashi, Tokyo; Tsutomu Kudo, Yokohama, all of Japan

[73] Assignee: Morinaga Milk Industry Co., Ltd., Tokyo, Japan

[21] Appl. No.: 722,106

[22] Filed: Apr. 11, 1985

[30] Foreign Application Priority Data

Apr. 18, 1984 [JP] Japan ................................ 59-76622

[51] Int. Cl.[4] ...................... A01N 63/00; A23C 9/12; C12N 1/04
[52] U.S. Cl. .................................... 424/93; 435/260; 435/252.1; 435/253.4; 426/61
[58] Field of Search ............... 435/182, 187, 188, 243, 435/252, 260; 424/93; 426/61; 427/213

[56] References Cited

U.S. PATENT DOCUMENTS 3,354,863 11/1967 Reynolds ............................. 118/62
3,477,864 11/1969 Tuji ..................................... 106/151
3,687,717 8/1972 Philip ................................. 427/213

FOREIGN PATENT DOCUMENTS 667201 11/1965 Belgium .
1151669 5/1969 United Kingdom .

OTHER PUBLICATIONS

Japanese Unexamined Patent Application Gazette 32221/1982.

Primary Examiner—Charles F. Warren
Assistant Examiner—Irene Marx
Attorney, Agent, or Firm—Jordan and Hamburg

[57] ABSTRACT

A grandular product is prepared by fluidizing core material such as saccharide in a granulating chamber, spraying melted binding material such as fat to the fluidized core material and concurrently feeding dried viable microorganism cells such as bifidobacterium towards the fluidized core material to form a granular product having stratified structure by adhering microorganism cells on the periphery of the core material. Since the product is prevented from permeation of atmospheric oxygen and environmental moisture, the cell survival rate of the product is higher than that of the conventional product during prolonged storage periods.

5 Claims, No Drawings

GRANULAR PRODUCT OF DRIED MICROORGANISM CELLS AND MANUFACTURING METHOD THEREFOR

TECHNICAL FIELD OF THE INVENTION

The invention relates to a granular product of stratified structure having higher viability for prolonged storage prepared from dried viable microorganism cells and a method for manufacturing thereof.

BACKGROUND OF THE INVENTION

It has been well known for a long time that oral administration of some viable bacteria or lactic acid bacteria to human beings and animals improve intestinal function and widely practiced to orally administer such viable microorganism for maintenance and promotion of health, for instance by adding these microorganisms to foodstuffs or feedstuffs. The various kinds of microorganisms are used for that purpose and various kinds of products containing them are known, for instance powder, granule, gel, liquid and so on. Recently, medical preparations, foodstuffs and feedstuffs containing lactic acid bacteria or bifidobacteria have held public attention.

It is, however, very difficult to preserve such product containing viable microorganism cells for a long time without decreasing cell survival rate, because the viability of these bacteria in this product decreases when environmental conditions are changed during storage. However, when such microorganism cells are preserved under the condition of lowered environmental moisture microorganism cells turn to resting cells and it is possible to store the microorganism cells for a long period.

Thus, cultivated and collected microorganism cells have hitherto been washed, added with a cryoprotectant, freeze-dried or vacuum-dried, pulverized, sifted out, added with starch or lactose as excipient and added with sugar or acidulant to obtain a powdered product. Such powdered products are often reprocessed after addition of suitable substances into granular or other block-type products. In the conventional method, it is important to keep moisture content of the product as low as possible during all the processing steps. However, it is not always easy to strictly keep such condition. Resting cells of microorganism are activated by the addition of water to dried microorganism cells in the step of processing or absorbing atmospheric moisture by the dried product for the period of storage. In this case, however, as the condition of survival for microorganism cells is extremely unsuitable, it is impossible to achieve sufficient viability of the microorganism cells.

It has been known that viability of the product containing dried microorganism cells during the storage period is effected by the presence of atmospheric oxygen, since free radicals are induced therein.

Therefore, it has been disclosed to suspend such dried viable microorganism cells in oil or fat for preventing permeation of environmental moisture (Japanese Unexamined Patent Application Gazette 2908/1981), to coat powder containing dried viable bifidobacteria with fat or oil for preventing permeation of environmental moisture and atmospheric oxygen (Japanese Unexamined Patent Application Gazette 33543/1982) and to pelletize a mixture of powder containing dried viable bifidobacteria with oil or fat for preventing permeation of environmental moisture and atmospheric oxygen which is used as a material to prepare various confections (Japanese Unexamined Patent Application Gazette 32221/1982).

According to the above prior arts, however, dried viable microorganism cells are only mixed with fat or oil or only suspended in fat or oil. Thus, powder particles of the prior art are not always completely coated with fat or oil and consequently the products prepared by the above prior methods do not achieve sufficient viability.

Futhermore, it has also been known to mix dried viable bifidobacteria with sufficiently dried starch in order to extremely decrease the water content thereof to prepare pelletized confections (Japanese Unexamined Patent Application Gazette 4976/1984). According to this prior method, however, it might be possible to decrease the water content in the product just after manufacturing thereof but it is almost impossible to keep the product from absorbing environmental moisture and atmospheric oxygen as it is. The product must be contained in a hermetically sealed container in which air is replaced with nitrogen. It goes without saying that such additional step and cost of additional material will occupy a considerable portion of the whole cost of the product.

The inventors have tried to overcome or improve the defects in this technical field to find a way for granulating dried viable microorganism cells without using any water and to produce a granule having a stratified structure like an onion and excellent viability.

SUMMARY

It is, thus, an object of the invention to provide a granular product containing dried viable microorganism cells, which prevents permeation of environmental moisture and atmospheric oxygen.

Another object is to provide a granular product containing dried viable microorganism cells which have excellent viability during a prolonged storage period.

A still further object is to provide a method for preparing a granular product containing dried viable microorganism cells by granulating without using any water which has excellent viability during a prolonged storage period.

These and other objects are attained by a granular product containing dried viable microorganism cells consisting of at least 0.1% by weight of a core material and less than 99.9% by weight of an adherent composition which comprises at least 5% by weight of a binding material substantially containing no water having a melting point of 25° to 60° C. and less than 95% by weight of dried viable microorganism cells, and having a stratified structure of said adherent composition surrounding said core material The present invention also relates to a process for manufacturing a granular product containing dried viable microorganism cells characterized by fluidizing core material in a granulating chamber and spraying melted binding material which contains substantially no water and concurrently feeding dried viable microorganism cells towards the fluidized core material to form a granular product of stratified structure by adhering said microorganism cells on a periphery of the core material.

DESCRIPTION OF THE PREFERRED EMBODIMENTS

The granular product according to the invention consists of a core material and an adherent material containing dried viable microorganism cells and binding material for coating said core material with said adherent material in a stratified structure.

As the core material, crystalline granulated sugar, a sugar/starch composition, particles prepared by pelletizing said materials, saccharide such as sucrose, lactose and glucose, acid crystals such as tartaric acid and citric acid, mixture thereof, particles prepared by pelletizing such acid crystals, and any other materials may be used so far as they are edible and have a hardness and size suitable as core of the nature referred to above. For instance, dried viable microorganism cells themselves, a pelletized product of such powder mixed with sugar or other additives prepared according to the prior art, and even a granular product prapared according to the invention may be used as the core material of the invention. The water content of the core material is preferably as low as possible, less than 5 weight %.

The core material may be used in an amount ranging from 0.1 weight % relative to the product up to such a considerably large amount that dried powder of microorganism is coated in a thin layer around the core, but from the practical view point it preferably ranges from 1 to 80 weight %.

As the binding material, fat and oil, lipid, emulsifier, glyceride, sorbitan fatty acid ester, propylene glycol fatty acid ester, sucrose fatty acid ester, paraffin, wax and any other materials or any mixture thereof may be used so far as it is edible and capable of exhibiting adhesion in the course of solidification of the melted binding material. It is necessary, however, that the binding material has a melting point ranging from 25° C. to 60° C. When the binding material has a melting point higher than 60° C., the granulating chamber will have to be kept at a temperature above 55° C., at which microorganisms are partly killed and partly so damaged as to be killed later. On the other hand, if the melting point of the binder is lower than 25° C., formed granules are apt to be agglomerated.

The amount of the binding material to be used in the invention is more than 5 weight %, and preferably ranges from 10 to 50 weight % based on the adherent material. When the amount is less than 5 weight %, sufficient adhesion cannot be attained so that desired granules are not formed or formed granules are easily collapsed due to lower hardness.

The strain of microorganism used in this invention is chosen depending on the use of the granular product or the purpose for manufacturing the product according to the invention. If it is intended to manufacture a granular product having improved intestinal function, known lactic acid bacteria belonging to the genus Lactobacillus, Leuconostoc and Streptococcus, and known bacteria belonging to the genus Bifidobacterium are preferably used. One or more bacteria which are normally found in the human or the animal intestinal tract are sometimes preferably added thereto. When manufacturing the granular product for production of silage, *Streptococcus faecalis* or *Lactobacillus plantarum* is preferably used.

The cultivated bacteria as referred to above are subjected to freeze-drying or vacuum drying according to the usual method. The obtained dried material may be crushed, sifted out and may be directly used for granulation, but a powdered mixture which is added with lactose, starch and other additives as excipient is preferably used. It is possible to control the number of viable microorganism cells in the powdered mixture by adjusting the amount of excipient to be added. The particle size of the powdered mixture is preferably below 100 mesh, and more preferably below 150 mesh.

The granular product prepared by the invention is concentric circles in section so as to form multi-layers of adherent material by adhering it around the core material. The outer surface of the granule may be coated with a desired material such as sugar, which is also one embodiment of the invention.

Characteristic features of the manufacturing process according to the invention will now be described. The adherent material in the amount of less than 99.9 weight % which comprises (1) a binding material having a 25°–60° C. melting point substantially containing no water (2) and dried viable microorganism cells is adhered to a fluidized core material of at least 0.1 weight % to form a granular product of stratified structure. The binding material of at least 5 weight % as one component of the adherent material is sprayed to the fluidized core material and concurrently dried viable microorganism cells of less than 95 weight % as the other component of the adherent material fed thereto. The temperature of the granulating chamber is adjusted depending on the properties of the binding material so that dried viable microorganism cells are adhered on the surface of the core material by and by in layers until reaching the desired size owing to adhesion of melted binding material to be gradually solidified.

In the process of the invention, thus, it is important to relevantly control the conditions of (1) fluidizing of the core, and (2) feeding temperature of the binding material and temperature of the granulating chamber.

In regard to fluidizing, it is necessary that the core material moves at a relevant fluidizing rate and suitable rotating rate in the granulating chamber so that dried viable microorganism cells may be uniformly adhered to the fluidizing core material without loss of adherent material by and by so as to form smooth spheres of stratified structure.

In order to realize such fluidizing condition, a centrifugal fluidizing method is preferably used. The apparatus for carrying out this method comprises a chamber having a plurality of slits for blowing air formed in the bottom of a peripheral wall which is mounted for rotation at the bottom of a granulating chamber so that core material and granulating particles coated with the adherent material are fluidized around the periphery of the chamber respectively with rotation by virtue of the centrifugal force caused by the rotation of the chamber aided by the agitating force of air blown through said slits.

In regard to the feeding temperature of the binding material the temperature of the granulating chamber, the melted binding material is fed through a conduit by means of a pump respectively heated so as to keep the binding material at a relevant temperature and in the melted state towards fluidizing core material respectively with rotation in the granulating chamber kept at a suitable temperature. When the temperatures are too low, the binding material is solidified so fast that the adhesive function of the binding material is not exhibited and consequently desired granules cannot be obtained. On the other hand, when the temperatures are too high, the binding material cannot be solidified or is solidified too late, and relevant adhesiveness is not available, so that desired granulation cannot be attained. In addition thereto, microorganism cells contacted with too hot a binding material are partly killed.

From the above, the feeding temperature of the binding material is preferably kept at the range of 35° to 75° C. which is 10° to 15° C. higher than the melting point of the binding material. The temperature in the granulating chamber is preferably kept at the range of 15°–55° C. which is 5° to 10° C. lower than the melting point of the binding material.

Control of the temperature in the granulating chamber may be carried out by adjusting the temperature of air blown out through the slits formed in the peripheral wall of the chamber.

It is possible to carry out further coating of desired material on the surface of the granular product according to the same method. Such coating is made for the purposes of preventing permeation of environmental mosisture and atmospheric oxygen, giving palatable taste, flavor and color and enteric coating. For example, the coating for preventing permeation of environmental moisture and atmospheric oxygen is carried out by using only binding material according to the present method. For enteric coating, shellac or zein is coated on the surface of the granular product by means of the same granulating apparatus. According to such coating the granular product of the invention is widely used for various purposes. It is also possible to combine vitamins, growth factors of intestinal flora and health foods with said core material, dried viable microorganism cells and binding material.

Some embodiments of the invention shall be given in reference to the following experiments and examples for the purpose of explaining the invention more definitely but not for limiting the scope of the invention.

EXPERIMENT 1

(Survival Rate of Microorganism Cells in the Granular Product)

Survival rates of microorganism cells in the granular products according to the invention without using any water in the granulating process and according to the conventional method where water or aqueous solution was used therefor were determined.

(a) Granular product of the invention (Sample No. 1);
This was prepared in the same manner as shown hereinbelow in Example 1.

(b) Granular product of control 1 (Sample No. 2)
This was prepared in the same manner as shown in Example 1, but as the binding material a 50% aqueous solution of sucrose was used instead of palmitic acid propyleneglycol ester of m.p. 35° C. Granular product obtained was dried and its moisture content was less than 4 weight %.

(c) Granular product of control 2 (Sample No. 3);
This was prepared as follows.

| Dried viable bifidobacteria cells used in Example 1 | 20 weight % |
| Corn starch | 50 weight % |
| Dried skim milk | 10 weight % |
| Aqueous solution of 50% sucrose | 20 weight % |

A pasty mixture obtained by blending the above components was granulated by means of a conventional screen extruder. The obtained granular product was dried and its moisture content was less than 4 weight %.

(d) Determination of cell survival rates;
For the three samples, the viable count of bifidobacteria in powder before granulation and in the granular product after granulation of the powder was determined according to the method of Mitsuoka et al. using BL agar culture medium ("Nihon Saikingaku Zasshi" (Japanese Journal of Bacteriology) Vol. 33, No. 6, Page 753 (1978)). Cell survival rates were calculated using the following equation (I).

Cell survival rate(%) = viable count of granular product × 100/(Viable count of powder × % of dried viable microorganism cells in the product/100) ... (I)

The results of this test are shown in Table 1.

TABLE 1

| Sample No. | Cell survival rate Sample | Survival rate (%) |
|---|---|---|
| 1 | Granular Product of Invention | 93 |
| 2 | Control 1 | 1.3 |
| 3 | Control 2 | 2.9 |

As will be seen from Table 1, it is definitely clear that the cell survival rate of the granular product of the invention in which granulation is carried out without using any water is remarkably higher than that of the products prepared by the prior art using water or aqueous solution.

EXPERIMENT 2

(Viability of the Granular Product)

The effects of atmospheric oxygen and environmental moisture on survival rates of bifidobacteria in the granular products prepared by the method of the present invention and the prior art were tested.

(a) Granular product of the invention (Sample No. 1);
This was prepared in the same manner as shown in Example 1.

(b) Granular product of control 1 (Sample No. 2);
This was prepared as follows.

| Dried viable bifidobacteria cells used in Example 1 | 50 weight % |
| Lactose | 15 weight % |
| Vegetable oil and fat (m.p. 39° C.) | 35 weight % |

A pasty mixture obtained by blending the above components was granulated by means of a conventional screen extruder.

(c) Tablet of control 2 (Sample No. 3);
This was prepared from the following.

| Dried viable bifidobacteria cells used in Example 1 | 10 weight % |
| Lactose (added for pelletizing) | 25 weight % |
| Dried corn starch | 5 weight % |
| Powdered sugar | 40 weight % |
| Dried skim milk | 18 weight % |
| Lubricant | 2 weight % |

The mixture of the above components was formed to a tablet by means of a conventional tableting machine.

(d) Effect of atmospheric oxygen

Each of samples 1, 2 and 3 was put into two hermetically sealed containers, one of which was filled with nitrogen gas to replace the air (oxygen absence) while the other as it was (oxygen presence). A total of six (6) containers were kept in an incubator at 37° C. for one month.

The viable count of bifidobacteria in the granular products before and after storage was determined by the same manner as in Experiment 1. Cell survival rate of each of the samples was calculated by the following equation (II).

Cell survival rate(%)=(Viable count of the sample after storage/Viable count of the sample before storage)×100 ... (II)

The results of this test are shown in Table 2.

TABLE 2

| | Effect of Atmospheric oxygen on cell | | |
|---|---|---|---|
| Sample No. | Sample | Gas in container | Survival Rate (%) |
| 1 | Invention | Air | 57 |
| | | Nitrogen | 60 |
| 2 | Control 1 | Air | 32 |
| | | Nitrogen | 58 |
| 3 | Control 2 | Air | 29 |
| | | Nitrogen | 59 |

As will be apparent from Table 2, there is no essential difference in the survival rates between the products of the invention which were preserved, in the presence and absence of oxygen. In contrast therewith, it is obviously recognized that the survival rates of Controls 1 and 2 were considerably affected with atmospheric oxygen. This means that the viable counts of bifidobacteria in these samples decreased extremely during storage. The granular product of the invention can be packed without replacing air in the container with nitrogen, which makes it possible to considerably lower the cost of the packed product according to the invention.

(e) Effect of environmental moisture

Each of Sample Nos. 1, 2 and 3 was put on a petri dish without cover and equilibrated with a saturated solution of potassium carbonate in a desiccator for one month at a temperature 37° C. and 43% of relative humidity.

The viable count of bifidobacteria in each of the samples before and after storage was determined by the same manner as in Experiment 1. Cell survival rate of each sample was calculated by above equation (II).

The results of this test are shown in Table 3.

TABLE 3

| | Effect of environmental moisture on cell | |
|---|---|---|
| Sample No. | Sample | Survival Rate (%) |
| 1 | Invention | 24.1 |
| 2 | Control 1 | 8.3 |
| 3 | Control 2 | 1.5 |

As will be seen from Table 3, the granular product of the invention shows excellent property for preventing permeation of atmospheric moisture in severe storage conditions in comparison with the products of the prior art. On the other hand, the granules of the Controls 1 and 2 were highly hygroscopic, changed to brownish color in appearance and decreased hardness during storage. Therefore, the granular products prepared by the prior art cannot be preserved for a long period of storage.

EXAMPLE 1

Three hundred grams of finely granulated sucrose (Trade name "NONPARREL 101" by Freund Sangyo Co., Ltd) of 14–20 mesh particle size as the core material was put into the granulating chamber of a centrifugal fluidizing granulator (Type CF-360 by Freund Sangyo Co., Ltd). By rotating the chamber and blowing air of 27°–30° C. from the slits formed in the peripheral wall, a fluidized core material was formed and the temperature of the chamber was kept at 27°–30° C.

Three hundred milliliters of propyleneglycol palmitic acid ester (m.p. 35° C.) as binding material was kept at about 50° C. and sprayed at a rate of 20 ml/min towards the fluidized core material. Concurrently, 1 kg of dried viable bifidobacteria (*Bifidobacterium longum* ATCC 15708) cells (The viable count bifidobacteria, $1.0 \times 10^{10}$/g) was fed through a screw-feeder to the fluidized core material for 15 minutes.

Thus, 1.5 kg granular product containing bifidobacteria was obtained, in which the mean particle diameter was about 1.7 mm and the mean particle weight was about 3.5 mg. The content of dried viable bifidobacteria in the granular product was 63.7% by weight and the viable count of bifidobacteria was $59 \times 10^8$/g. The cell survival rate calculated from above equation (I) was about 93%.

EXAMPLE 2

Five hundred grams of the granular product prepared in the same manner as in Example 1 was fluidized in a centrifugal fluidizing granulator as in Example 1, under a controlled temperature of 30°–32° C. in the granulating chamber. Three hundred milliliters of 5% (W/V) ethanolic solution of shellac was sprayed towards the fluidized granular product at a rate of 10 ml/min to coat the granular product with shellac. 500 ml of 5% (W/V) ethanolic solution of zein was then sprayed towards the fluidized granular product at a rate of 10 ml/min. The product was then dried in a vacuum at 30° C. for 6 hours to obtain a granular product coated with shellac and zein. About 520 g of final product having 7.4% by weight of the coating material and $48 \times 10^8$/g in viable count of bifidobacteria was obtained. The cell survival rate calculated by following equation was about 88%.

Cell survival rate(%)=(Viable count of sample after coating/Viable count of sample before coating)×100.

EXAMPLE 3

Three hundred grams of finely granulated sucrose (same substance as Example 1) of 20 to 24 mesh in particle size as a core material was put into the granulating chamber of Example 1. The core material was fluidized by blowing air from the slits with controlling volume and temperature thereof, and the temperature in the chamber was kept at 32°–35° C. Five hundred milliliters of vegetable fat (m.p. 42° C.) kept at a temperature of about 55° C. was sprayed towards the fluidized core material at a rate of 20 ml/min. Concurrently, 1 kg of dried viable lactic acid bacteria (Streptococcus faecium ATTCC 8043) cells (viable count of said bacteria: $25 \times 10^8$/g) was fed through the screw feeder to the fluidized core material for about 25 minutes.

About 1.7 kg of granular product having about 1.5 mm mean particle diameter and about 2.9 mg mean particle weight was obtained. The final product contained 57.1% by weight of dried lactic acid bacteria cells.

The viable count of bacteria in the final product was determined by the method for testing the viable count of lactic acid bacteria ("Standard Methods of Analysis for Hygienic Chemists—With Commentary", page 257, Edited by Pharmaceutical Society of Japan, Published by Kinbara Publishing Co., Ltd., (1980)) to be $14 \times 10^8$/g. The cell survival rate calculated frour above equation (I) was about 98%.

What is claimed is:

1. A granular product containing dried viable bacterial cells consisting of 1 to 80% by weight of a core material and 20 to 99% by weight of an adherent composition, the adherent composition comprising at least 5% by weight of a binding material containing substantially no water having a melting point of 25° to 60° C. and less than 95% by weight of dried viable bacterial cells selected from the genera Bifidobacterium and lactic acid Streptococcus, and having smooth spheres of a stratified structure of said adherent composition surrounding said core material.

2. A granular product according to claim 1, wherein said granular product is further coated with at least one coating agent selected from the group consisting of an agent preventing permeation of atmospheric oxygen, an agent preventing permeation of environmental moisture and an enteric coating agent.

3. A granular product according to claim 2, wherein said coating agent is selected from the group consisting of shellac and zein.

4. A granular product according to claim 1, wherein said core material is selected from the group consisting of saccharide, dried viable microorganism cells, granules containing dried viable microorganism cells as a main component, capsules containing dried viable microorganism cells as a main component, tablets containing dried viable microorganism cells as a main component and mixtures thereof, said dried viable microorganism cells being dried viable bacteria cells selected from the genera Bifidobacterium and lactic acid Streptococcus.

5. A granular product according to claim 1, wherein said binding material is selected from the group consisting of natural fat, synthetic glyceride, "emulsifier which are not natural fats or synthetic glycerides", paraffin and mixtures thereof.

* * * * *